(12) United States Patent
Tung

(10) Patent No.: US 6,361,169 B1
(45) Date of Patent: Mar. 26, 2002

(54) SYSTEM AND METHOD FOR ORTHOKERATOLOGY

(76) Inventor: Hsiao-Ching Tung, 2F, No. 164, Ling Jiang Street, Taipei (TW)

(*) Notice: Subject to any disclaimer, the term of this patent is extended or adjusted under 35 U.S.C. 154(b) by 0 days.

(21) Appl. No.: 09/591,913

(22) Filed: Jun. 9, 2000

(51) Int. Cl.⁷ .................................................. A61B 3/00
(52) U.S. Cl. ........................................................ 351/219
(58) Field of Search ................................. 351/219, 216, 351/246, 247, 177; 424/400, 429; 514/839; 606/4, 5

(56) References Cited

U.S. PATENT DOCUMENTS 6,132,735 A * 10/2000 Harris et al. ................. 424/400

* cited by examiner

Primary Examiner—George Manuel
(74) Attorney, Agent, or Firm—Philip K. Yu

(57) ABSTRACT

The present invention provides a method for selecting a contact lens for orthokeratology. The method comprises selecting an appropriate contact lens based on the patient's ocular information using a vision improvement program reference table and fitting the patient with the selected vision improvement lens.

27 Claims, 1 Drawing Sheet

REFERENCE TABLE

| Mean K/ S.E | -1.50 | -2.00 | -2.50 | -3.00 | -3.50 | -4.00 | -4.50 | -5.00 |
|---|---|---|---|---|---|---|---|---|
| 39.74-40.00 | A001 | A002 | A003 | A004 | A005 | A006 | A007 | A008 |
| 40.01-40.26 | B001 | B002 | B003 | B004 | B005 | B006 | B007 | B008 |
| 40.27-40.52 | C001 | C002 | C003 | C004 | C005 | C006 | C007 | C008 |
| 40.53-40.78 | D001 | D002 | D003 | D004 | D005 | D006 | D007 | D008 |
| 40.79-41.04 | E001 | E002 | E003 | E004 | E005 | E006 | E007 | E008 |
| 41.05-41.30 | F001 | F002 | F003 | F004 | F005 | F006 | F007 | F008 |
| 41.31-41.56 | G001 | G002 | G003 | G004 | G005 | G006 | G007 | G008 |
| 41.57-41.82 | H001 | H002 | H003 | H004 | H005 | H006 | H007 | H008 |
| 41.83-42.08 | I001 | I002 | I003 | I004 | I005 | I006 | I007 | I008 |
| 42.09-42.33 | J001 | J002 | J003 | J004 | J005 | J006 | J007 | J008 |
| 42.34-42.59 | K001 | K002 | K003 | K004 | K005 | K006 | K007 | K008 |
| 42.60-42.85 | L001 | L002 | L003 | L004 | L005 | L006 | L007 | L008 |
| 42.86-43.09 | M001 | M002 | M003 | M004 | M005 | M006 | M007 | M008 |
| 43.10-43.35 | N001 | N002 | N003 | N004 | N005 | N006 | N007 | N008 |
| 43.36-43.61 | O001 | O002 | O003 | O004 | O005 | O006 | O007 | O008 |
| 43.62-43.86 | P001 | P002 | P003 | P004 | P005 | P006 | P007 | P008 |
| 43.87-44.11 | Q001 | Q002 | Q003 | Q004 | Q005 | Q006 | Q007 | Q008 |
| 44.12-44.36 | R001 | R002 | R003 | R004 | R005 | R006 | R007 | R008 |
| 44.37-44.61 | S001 | S002 | S003 | S004 | S005 | S006 | S007 | S008 |
| 44.62-44.86 | T001 | T002 | T003 | T004 | T005 | T006 | T007 | T008 |
| 44.87-45.10 | U001 | U002 | U003 | U004 | U005 | U006 | U007 | U008 |
| 45.11-45.35 | V001 | V002 | V003 | V004 | V005 | V006 | V007 | V008 |
| 45.36-45.60 | W001 | W002 | W003 | W004 | W005 | W006 | W007 | W008 |
| 45.61-45.84 | X001 | X002 | X003 | X004 | X005 | X006 | X007 | X008 |
| 45.85-46.09 | Y001 | Y002 | Y003 | Y004 | Y005 | Y006 | Y007 | Y008 |
| 46.10-46.33 | Z001 | Z002 | Z003 | Z004 | Z005 | Z006 | Z007 | Z008 |
| Over 46.34 | | | | | | | | |

COLOR CODING:

ONE

TWO

CUSTOM MADE

Figure 1

REFERENCE TABLE

| Mean K/ S.E | -1.50 | -2.00 | -2.50 | -3.00 | -3.50 | -4.00 | -4.50 | -5.00 |
|---|---|---|---|---|---|---|---|---|
| 39.74-40.00 | A001 | A002 | A003 | A004 | A005 | A006 | A007 | A008 |
| 40.01-40.26 | B001 | B002 | B003 | B004 | B005 | B006 | B007 | B008 |
| 40.27-40.52 | C001 | C002 | C003 | C004 | C005 | C006 | C007 | C008 |
| 40.53-40.78 | D001 | D002 | D003 | D004 | D005 | D006 | D007 | D008 |
| 40.79-41.04 | E001 | E002 | E003 | E004 | E005 | E006 | E007 | E008 |
| 41.05-41.30 | F001 | F002 | F003 | F004 | F005 | F006 | F007 | F008 |
| 41.31-41.56 | G001 | G002 | G003 | G004 | G005 | G006 | G007 | G008 |
| 41.57-41.82 | H001 | H002 | H003 | H004 | H005 | H006 | H007 | H008 |
| 41.83-42.08 | I001 | I002 | I003 | I004 | I005 | I006 | I007 | I008 |
| 42.09-42.33 | J001 | J002 | J003 | J004 | J005 | J006 | J007 | J008 |
| 42.34-42.59 | K001 | K002 | K003 | K004 | K005 | K006 | K007 | K008 |
| 42.60-42.85 | L001 | L002 | L003 | L004 | L005 | L006 | L007 | L008 |
| 42.86-43.09 | M001 | M002 | M003 | M004 | M005 | M006 | M007 | M008 |
| 43.10-43.35 | N001 | N002 | N003 | N004 | N005 | N006 | N007 | N008 |
| 43.36-43.61 | O001 | O002 | O003 | O004 | O005 | O006 | O007 | O008 |
| 43.62-43.86 | P001 | P002 | P003 | P004 | P005 | P006 | P007 | P008 |
| 43.87-44.11 | Q001 | Q002 | Q003 | Q004 | Q005 | Q006 | Q007 | Q008 |
| 44.12-44.36 | R001 | R002 | R003 | R004 | R005 | R006 | R007 | R008 |
| 44.37-44.61 | S001 | S002 | S003 | S004 | S005 | S006 | S007 | S008 |
| 44.62-44.86 | T001 | T002 | T003 | T004 | T005 | T006 | T007 | T008 |
| 44.87-45.10 | U001 | U002 | U003 | U004 | U005 | U006 | U007 | U008 |
| 45.11-45.35 | V001 | V002 | V003 | V004 | V005 | V006 | V007 | V008 |
| 45.36-45.60 | W001 | W002 | W003 | W004 | W005 | W006 | W007 | W008 |
| 45.61-45.84 | X001 | X002 | X003 | X004 | X005 | X006 | X007 | X008 |
| 45.85-46.09 | Y001 | Y002 | Y003 | Y004 | Y005 | Y006 | Y007 | Y008 |
| 46.10-46.33 | Z001 | Z002 | Z003 | Z004 | Z005 | Z006 | Z007 | Z008 |
| Over 46.34 | | | | | | | | |

COLOR CODING:

ONE

TWO

CUSTOM MADE

Figure 1

SYSTEM AND METHOD FOR ORTHOKERATOLOGY

FIELD OF THE INVENTION

The present invention is directed to a system and method for selecting an appropriate contact lens in orthokeratology.

BACKGROUND OF THE INVENTION

Orthokeratology has been practiced since the 1960's and involves reduction, elimination, or modification (including controlled progression) of myopia by a programmed application of contact lenses. Unlike the typical contact lenses for vision correction which are worn during day time, in orthokeratology corneas are reshaped by wearing contact lenses overnight. This reshaping of corneas reduces or eliminates a need for wearing glasses or contact lenses during the day.

Currently, the shape of contact lenses are generally individually designed by doctors for each patients. The lenses are then ordered through a laboratory which custom makes the lenses based on the parameters provided by the doctor. The lenses are then delivered to the doctor for fitting on the patient. This requires the patient to wait days, and sometimes weeks, from the time the patient is examined by the doctor to when the patient is finally fitted with the lenses. If the lenses do not fit properly, the processes are repeated, thereby creating more delays. Delays between the initial examination and fitting of the lenses may increase the cost and cause inconvenience to the patient in that the patient has to have at least two separate appointments with the doctor to be fitted with contact lenses for orthokeratology.

Therefore, there is a need for a simple system and a method for doctors in selecting and fitting a patient with contact lenses for orthokeratology which reduces or eliminates delays.

SUMMARY OF THE INVENTION

The present invention provides a system and a method for selecting a contact lens for orthokeratology comprising selecting an appropriate contact lens based on the ocular information using a vision improvement program reference table, and fitting the patient with the selected vision improvement lens. The vision improvement program reference table includes a plurality of mean corneal curvature values, a plurality of range of ratios between the mean corneal curvature and a spherical equivalent value, and a listing of appropriate contact lenses corresponding to these values.

Preferably, a doctor is provided with a plurality of contact lenses which corresponds to at least a significant portion of the number of contact lenses listed in the vision improvement program reference table. In this manner, the doctor is able to select an appropriate contact lens for a patient from the plurality of contact lenses which are readily available, thereby eliminating or significantly reducing the number of custom made lenses that are required.

BRIEF DESCRIPTION OF THE DRAWINGS

FIG. 1 is an illustrative example of a vision improvement program reference table, i.e., chart or matrix, containing mean corneal curvature values, ranges of ratio between the mean corneal curvature and a spherical equivalent value, and identification codes for appropriate contact lenses corresponding to these values.

DETAILED DESCRIPTION OF THE INVENTION

The present invention provides a system and a method for reducing the amount of or eliminating the need for a practitioner of the present invention to custom fit the contact lenses in a patient for orthokeratology. In order to determine the shape of contact lenses required for orthokeratology, knowledge of a patient's topical surface area of the cornea is generally required. It should be appreciated that in order to practice the methods of the present invention, a practitioner of the present invention (e.g., an optometrist or an ophthalmologist) should be familiar with orthokeratology, rigid gas permeable (RGP) lenses, and four curve lenses. Therefore, it is to be understood that the present disclosure assumes the practitioner of the present invention has the necessary knowledge and training in orthokerotology.

Orthokeratology is a method of improving vision using contact lenses to reshape the cornea of a patient. Previous orthokeratology used 3 curve lenses. However, these lenses were able to correct only minor vision problems. Introduction of 4 curve lenses in the mid 1990's allowed correction of vision defects up to about 4.00–5.00 Diopters. Most lenses are designed by a doctor examining the patient and the parameters for the lenses are then sent to a laboratory which custom manufactures the lenses for each patients. This method of custom manufacturing each individual lenses results in delays and sometimes added costs to the patient. The present invention reduces or eliminates a need for custom manufacturing lenses for orthokeratology by providing a plurality of contact lenses along with a vision improvement program table (i.e., matrix or chart) which identifies a particular lens for a given ocular information of a patient.

As used herein, the term "plurality of lenses" refers to providing at least about 70% of the lenses corresponding to the chart, preferably at least about 80% of the lenses and more preferably at least about 90% of the lenses and most preferably about 100% of the lenses. In this manner, the practitioner of the present invention (e.g., a doctor) has a broad selection of lenses to choose from for each individual patient. Moreover, the practitioner of the present invention may be provided with multiple sets of lenses corresponding to popular lens parameters.

The term "# curve lenses" indicates contact lenses having the indicated number (i.e., #) of concentric curves.

Preferably, contact lenses (i.e., "lenses") are 3 to 6 curve contact lenses comprising one central optical zone, 1 to 3 intermediate peripheral zone, and one peripheral zone. The primary purpose of the central optical zone is to function as a contact area for hydraulic massage. Intermediate peripheral zones are steeper than the optical zone to allow alignment to cornea and tear exchange under the lens. Moreover, lenses are designed according to the common cornea shape of human eyes to allow maximum successful fitting rate. Preferably, lenses are designed based on a calculation according to the sagittal depth and arranged by continuous progression from flattest cornea (e.g., 39.00D) to steepest cornea (e.g., 50.00D). Powers are also calculated, preferably, to cover the most common myopia.

By using a standardized manufacturing and dispensing system, necessity of custom made lenses are eliminated or significantly reduced. Preferably, the plurality of lenses (i.e., inventory lenses) are arranged in a similar arrangement to that of the vision improvement program chart to allow suitable lenses to be found efficiently. Moreover, by allowing lenses to be ordered through a variety of means such as telephone, mail order, through internet, and combinations thereof, one can practice the present invention using a variety of forms of commerce including, "e-commerce".

As illustrated in FIG. 1, the vision improvement program chart of the present invention comprises information such as mean corneal curvatures (i.e., Km), refraction data (i.e., S.E. or spherical equivalent values), and a listing of appropriate contact lenses corresponding to these values. For the ease of lens identification, the listing of lenses are, preferably, provided in codes, e.g., product codes. The chart lists lenses (or provides codes for lenses) with sagittal depth of 3 to 6 curve lenses, preferably 4 and 5 curve lenses, which corresponds to the sagittal depth of the cornea curvature.

It should be appreciated that as with any other medical procedure, the patient must first be evaluated by a person skilled in the art of vision correction (e.g., optometrist or ophthalmologist) in order to determine whether the patient is a suitable candidate for orthokerotology. Thus, the first evaluation is to determine whether the patient has myopia and/or astigmatism which can be corrected with orthokerotology. Once the need for orthokerotology is determined, further evaluation is made to determine whether the patient's eyes are suitable for contact lenses. For example, patients with dry eyes, scarring on the cornea and/or patients who have allergic reactions are typically not well suited for orthokerotology; however, the practitioner of the present invention should evaluate each patient in a case-by-case basis. All of the above described ocular information are collected and evaluated prior to prescribing the patient with orthokerotology.

The present invention will now be illustrated using vision improvement program chart of FIG. 1. A patient's Km in diopters, preferably up to 2 decimal places, is calculated as follows:

Km=(steep K+flat K)/2, the average of steep and flat kerotometer reading.

S.E.=Spherical power−(K astigmatism)/2, where Spherical power is expressed in minus cylinder, K astigmatism= steep K−flat K (in diopters). Final selection of S.E. is based on rounding down. For example, −3.00, −3.25 and −3.49 all results in selecting column −3.00, whereas −3.50 results in column −3.50. For example, determination of proper lenses for a patient having K=42.62×44.50 @ 90, and spherical refraction of −4.50−1.75×180 is as follows:

Km=(42.62+44.50)/2=43.56

K astigmatism=44.50−42.62=1.88

S.E.=−4.50−1.88/2=−4.50−0.94=−5.44

Thus, the final selection of lenses for this patient is defined by Km Row "O" and S.E. Column "O008."

In cases where the patient's refraction is greater than −5.50, inventory lenses can be used as trial lenses. After trial fitting the correct Km lenses and performing an over refraction, the final custom lenses may be ordered. If only nightwear option is utilized, column 008 lenses can be directly dispensed without power adjustments.

The vision improvement chart in FIG. 1 is arranged from flattest (A) to steepest (Z) Km values. While trial fitting lenses, choosing lenses up or down in the same letter column allows fitting adjustments. In some cases, fine-tuning lenses may require two steps or more in letter changes before different fluorescein patterns can be observed. While not necessary to achieve a good orthokerotology result, an ideal fit lens will have bulls eye fluorescein pattern, good centration and about 0.1 mm movement with patient's eye blink.

After selecting an appropriate lens, practitioner of the present invention determines a proper fit of the lens (e.g., checking the tears and fitting of the lenses on the cornea) using any of the variety of methods currently available such as, for example, fluorescein pattern testing. Based on the results of a fitting test, the practitioner of the present invention may make adjustment to use steeper lenses or flatter lenses. Typically, the chart in FIG. 1 is used to select initial set of lenses based on the patient's Km and S.E. values. The patient is then provided with a schedule or an instruction for wearing the lenses for a particular duration (e.g., wearing lenses prior to or during the patient's bed time).

In one particular embodiment of the present invention, at least about 75% of patients, preferably 85% of the patients, may covered by the inventory of about 168 lenses. Thus, methods of the present invention eliminate or reduce the number of custom made lenses, thereby eliminating a waiting period for the lens order to be filled by a laboratory. Moreover, because a plurality of lenses is provided, in most cases the practitioner of the present invention is able to custom fit the lenses to a patient.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method for selecting a contact lens for orthokeratology comprising:
    selecting an appropriate contact lens based on the ocular information using a vision improvement program reference table; and
    fitting the patient with the selected vision improvement lens,
    wherein said vision improvement program reference table comprises:
        (a) a plurality of mean corneal curvature values;
        (b) a plurality spherical equivalent values.

2. The method of claim 1 further comprising the steps of determining a proper fit of the selected vision improvement lens on the patient.

3. The method of claim 2, wherein said proper fit determination step comprises checking the tears and fitting of the lens on the cornea of the patient.

4. The method of claim 2, wherein said proper fit determination step comprises fluorescein pattern test.

5. The method of claim 1, wherein the lens is selected from a plurality of contact lenses.

6. The method of claim 1 further comprising determining ocular information of a patient prior to said step of selecting the contact lens.

7. The method of claim 6, wherein the ocular information comprises a corneal curvature value and refraction data.

8. The method of claim 7, wherein the refraction data comprises spherical equivalent value.

9. The method of claim 7, wherein the corneal curvature value is mean corneal curvature value.

10. The method of claim 7, wherein the ocular information further comprises ocular health of the patient.

11. The method of claim 10 further comprising determining whether the ocular health of the patient is suitable for using the contact lens.

12. The method of claim 1, wherein the contact lens is capable of reshaping the patient's cornea.

13. The method of claim 12, wherein the contact lens is worn by the patient during a sleep period.

14. The method of claim 12, wherein the contact lens comprises a plurality of curves.

15. The method of claim 1, wherein the lens is selected from a plurality of contact lenses.

16. A method for reshaping cornea of a patient comprising:

determining ocular information of the patient;

selecting an appropriate contact lens based on the ocular information using a vision improvement program reference table; and fitting the patient with the selected contact lens, wherein the ocular information comprises mean corneal curvature value and spherical equivalent value.

17. The method of claim 16, wherein the ocular information further comprises ocular health of the patient.

18. The method of claim 17 further comprising determining whether the ocular health of the patient is suitable for using the contact lens.

19. The method of claim 16 further comprising the steps of determining a proper fit of the selected contact lens on the patient.

20. The method of claim 19, wherein said proper fit determination step comprises checking the tears and fitting of the contact lens on the cornea of the patient.

21. A reference table for selecting an appropriate contact lens for orthokeratology comprising:

(a) a plurality of mean corneal curvature values;

(b) a plurality of range of ratios between the mean corneal curvature and a spherical equivalent value; and (c) a listing of appropriate contact lenses corresponding to the values of (a) and (b).

22. The reference table of claim 21 further comprising a color coding scheme for indicating a plurality of inventory control methodologies.

23. The reference table of claim 21, wherein the mean corneal curvature value is from about 39.74 Diopter to about 46.34 Diopter.

24. The reference table of claim 21, wherein the listing of contact lenses comprises codes corresponding to particular contact lenses.

25. An orthokeratology kit comprising a chart for selecting an appropriate contact lens and a plurality of contact lenses, wherein said chart comprises:

(a) a plurality of mean corneal curvature values;

(b) a plurality of range of ratios between the mean corneal curvature and a spherical equivalent value; and (c) a listing of appropriate contact lenses corresponding to the values of (a) and (b).

26. The orthokeratology kit of claim 25, wherein the mean corneal curvature value is from about 39.74 Diopter to about 46.34 Diopter.

27. The orthokeratology kit of claim 25, wherein the listing of contact lenses comprises codes corresponding to a particular contact lenses.

* * * * *